(12) United States Patent
Neelakantan et al.

(10) Patent No.: US 12,092,597 B2
(45) Date of Patent: Sep. 17, 2024

(54) ARYLPHOSPHINE NANOMATERIAL CONSTRUCTS FOR MOISTURE-INSENSITIVE FORMALDEHYDE GAS SENSING

(71) Applicant: Palo Alto Research Center Incorporated, Palo Alto, CA (US)

(72) Inventors: Ravi Neelakantan, San Francisco, CA (US); Rahul Pandey, San Jose, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 398 days.

(21) Appl. No.: 17/541,768

(22) Filed: Dec. 3, 2021

(65) Prior Publication Data

US 2023/0175999 A1 Jun. 8, 2023

(51) Int. Cl.
*G01N 27/12* (2006.01)
*G01N 33/00* (2006.01)

(52) U.S. Cl.
CPC ....... *G01N 27/125* (2013.01); *G01N 33/0036* (2013.01)

(58) Field of Classification Search
CPC .......................... G01N 27/125; G01N 33/0036
See application file for complete search history.

(56) References Cited

U.S. PATENT DOCUMENTS

| | | | | |
|---|---|---|---|---|
| 2003/0171523 | A1* | 9/2003 | Lachowicz | C08F 22/1006 526/319 |
| 2004/0147555 | A1* | 7/2004 | Fujimoto | C07D 211/72 514/317 |
| 2018/0038822 | A1* | 2/2018 | Momose | G01N 27/125 |
| 2018/0292340 | A1* | 10/2018 | Koenig | G01N 27/124 |
| 2019/0250114 | A1* | 8/2019 | Kamin | G01N 27/125 |
| 2020/0049646 | A1* | 2/2020 | Logan | G01N 27/407 |
| 2020/0276560 | A1* | 9/2020 | Leung | B01J 37/0018 |
| 2021/0208731 | A1* | 7/2021 | Hu | G02F 1/13338 |

* cited by examiner

*Primary Examiner* — Jermele M Hollington
*Assistant Examiner* — Zannatul Ferdous
(74) *Attorney, Agent, or Firm* — Vorys, Sater, Seymour and Pease LLP (57) ABSTRACT

Sensors for detecting a formaldehyde-containing gas may include a first electrode and a second electrode; and an arylphosphine nanomaterial construct disposed between the first electrode and the second electrode, the arylphosphine nanomaterial construct including single-walled carbon nanotubes; and an arylphosphine including at least one aryl group. Methods for detecting formaldehyde include exposing a sensor to a formaldehyde-containing gas, the sensor including a first electrode and a second electrode; and an arylphosphine nanomaterial construct disposed between the first electrode and the second electrode, the arylphosphine nanomaterial construct including single-walled carbon nanotubes; and an arylphosphine containing at least one aryl group; monitoring a resistance between the first electrode and the second electrode; and determining a formaldehyde concentration from the resistance.

20 Claims, 4 Drawing Sheets

ARYLPHOSPHINE NANOMATERIAL CONSTRUCTS FOR MOISTURE-INSENSITIVE FORMALDEHYDE GAS SENSING

FIELD

The present disclosure generally relates to gas sensors for detecting formaldehyde and methods for making and using the same.

BACKGROUND

Formaldehyde is a naturally occurring volatile organic compound (VOC) and an important precursor in the production of materials with commercial and residential applications. Like many VOCs, formaldehyde is toxic and a recognized carcinogen. The United States National Institute for Occupational Safety and Health (NIOSH) considers 20 ppm formaldehyde in the atmosphere to be immediately dangerous to life and health (IDLH). Similarly, the Occupation Safety and Health Administration (OSHA) has established a permissible exposure limit (PEL) for formaldehyde in the workplace at 0.75 parts formaldehyde per million parts of air (0.75 ppm) measured as an 8-hour time-weighted average (TWA). Other agencies and organizations have recommended that the acceptable level be reduced to less than about 0.10 ppm (100 ppb).

Gas sensors may be utilized to quantify environmental formaldehyde concentrations emitted from processes and products to ensure compliance with regulatory guidelines and general health considerations. Despite the desirability of monitoring formaldehyde concentrations using a gas sensor, doing so can be less than straightforward in many instances. While generally effective for measuring high formaldehyde concentrations in controlled settings, current gas sensors lack capabilities to measure low formaldehyde concentrations and are expensive for widespread use. Current sensor designs are also frequently susceptible to interference and deactivation by common humidity levels, which may require sensor maintenance or drying samples prior to measurement. For example, gas sensors incorporating metal oxide semiconductors may have detection sensitivities below 100 ppb in ambient conditions, however, such designs have high power consumption rates and operational temperatures.

SUMMARY

The present disclosure provides gas sensors for detecting formaldehyde and methods for making and using the same.

In one aspect, sensors for detecting a formaldehyde-containing gas may include a first electrode and a second electrode; and an arylphosphine nanomaterial construct disposed between the first electrode and the second electrode, the arylphosphine nanomaterial construct including single-walled carbon nanotubes and an arylphosphine including at least one aryl group.

In another aspect, methods for constructing a gas sensor for detecting formaldehyde include: combining an arylphosphine with a suspension of single-walled carbon nanotubes to produce an arylphosphine nanomaterial construct; and depositing the arylphosphine nanomaterial construct between a first electrode and a second electrode.

In another aspect, methods for detecting formaldehyde include exposing a sensor to a formaldehyde-containing gas, the sensor including a first electrode and a second electrode; and an arylphosphine nanomaterial construct disposed between the first electrode and the second electrode, the arylphosphine nanomaterial construct including single-walled carbon nanotubes and an arylphosphine containing at least one aryl group; monitoring a resistance between the first electrode and the second electrode; and determining a formaldehyde concentration from the resistance.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and having the benefit of this disclosure.

DETAILED DESCRIPTION

The present disclosure generally relates to gas sensors for detecting formaldehyde and methods for making and using the same. Particularly, the present disclosure is directed to the preparation of arylphosphine nanomaterial constructs and their incorporation as sensing elements within a gas sensor for detecting formaldehyde, and methods of utilizing such gas sensors to quantify formaldehyde concentrations.

Sensors disclosed herein utilize a sensing element placed between at least two electrodes that collectively define a circuit capable of measuring a proportional change in resistance/conductance upon interaction with a selected analyte, such as formaldehyde. When formaldehyde gas adsorbs to the sensing element, the electronic state of the sensing element is changed to afford a corresponding change in resistance that is proportional to the amount of formaldehyde adsorbed. The change in resistance can be measured by any suitable technique and calibrated against known formaldehyde concentrations.

Sensing elements based on conductive nanomaterials, such as carbon nanotubes (CNTs), may interact with an analyte (e.g., formaldehyde) directly without the conductive nanomaterial being further functionalized, or the conductive nanomaterial may be functionalized (covalently and/or non-covalently) with various compounds having further affinity for a selected analyte (e.g., formaldehyde) through various chemical interactions (e.g., hydrogen bonding, electrophilic/nucleophilic interaction, ionic bonding, and the like). The conductive nanomaterial may transmit current between the electrodes, and the change in resistance during this process may be influenced by the quantity of formaldehyde that has interacted with the compound functionalizing the conductive nanomaterial.

Current sensors that utilize conductive nanomaterials for detecting formaldehyde typically incorporate nanomaterials functionalized with amines, alcohols, or organic acids that interact with formaldehyde through hydrogen bonding to promote a measurable change in the electronic state (e.g., resistivity or conductivity) of the sensing element. However, competing hydrogen donors, including water vapor and other ubiquitous gases, can saturate and/or inactivate such sensors. Consequently, sensors incorporating conductive nanomaterials functionalized with amines, alcohols, or organic acids may lose sensitivity and/or become inactivated at relative humidity (RH) values above about 20%, a very low value. The excessive moisture sensitivity ultimately limits the usefulness of these devices, because formaldehyde gas concentrations may be 1 ppm or lower, while the indoor RH values may exceed 40% for most residential or commercial environments where exposure detection is critical. As such, such conventional sensors may be incapable of detecting low concentrations of formaldehyde and changes in the amount thereof.

Sensors disclosed herein utilize sensing elements that may detect formaldehyde through interaction of the sensing elements with the electrophilic carbonyl carbon of the formaldehyde, which reduces interference from competing hydrogen bond donors and may increase sensitivity in humid environments. Particularly, sensing elements may feature conductive nanomaterials associated with and/or functionalized with groups such as phosphines, which have poor proton affinity (reduced hydrogen bonding), low water solubility, weak basicity, and high nucleophilicity for electron-deficient carbonyl carbons. Surprisingly, incorporation of such nucleophilic groups that are not hydrogen bond donors or acceptors upon the conductive nanomaterial of the sensing element also may afford a different resistance response in comparison to other types of gas sensors. In particular, comparative gas sensors functioning through hydrogen bond formation may register an increase in resistance with increasing formaldehyde concentrations. In contrast, the gas sensors disclosed herein may register a decrease in resistance (increase in conductivity) when increasing concentrations of formaldehyde are interacted with the sensing element via the carbonyl carbon of formaldehyde. The resulting increased sensitivity provides gas sensors that are relatively simple in construction, low-cost, and exhibit minimal interference from water vapor.

Advantageously, gas sensors disclosed herein for detecting formaldehyde may be compact devices with low power consumption, and offer applicability for widespread environmental monitoring applications, even in relatively humid environments. Gas sensors disclosed herein are capable of operation at room temperature and may be utilized to detect formaldehyde concentrations of about 100 ppb or below. In some embodiments, the gas sensors may be capable of detecting formaldehyde in a range of about 50 ppb to about 800 ppb, although higher concentrations may also be detected. Further advantageously, the gas sensors disclosed herein may be operable at ambient conditions and a relative humidity (RH) from about 0% to about 90%, or even higher, while still remaining effective for detecting low concentrations of formaldehyde. In some embodiments, gas sensors disclosed herein may be capable of detecting formaldehyde at a relative humidity of about 20% or greater at room temperature. As used herein, the term "ambient conditions" refers to a temperature of 20±5° C. and a pressure of 1±0.1 atmospheres (atm). The gas sensors may also perform suitably over temperature ranges outside ambient conditions in some embodiments, such as over a range of about −5° C. to about 50° C., for example.

Sensors of the present disclosure may comprise: a first electrode and a second electrode, and an arylphosphine nanomaterial construct disposed between the first electrode and the second electrode. The arylphosphine nanomaterial construct comprises single-walled carbon nanotubes, and an arylphosphine comprising at least one aryl group. Further details regarding the single-walled carbon nanotubes and the arylphosphine are provided below. Other conductive nanomaterials may alternately be substituted for single-walled carbon nanotubes or be mixed with single-walled carbon nanotubes, according to some embodiments.

Figure 1:
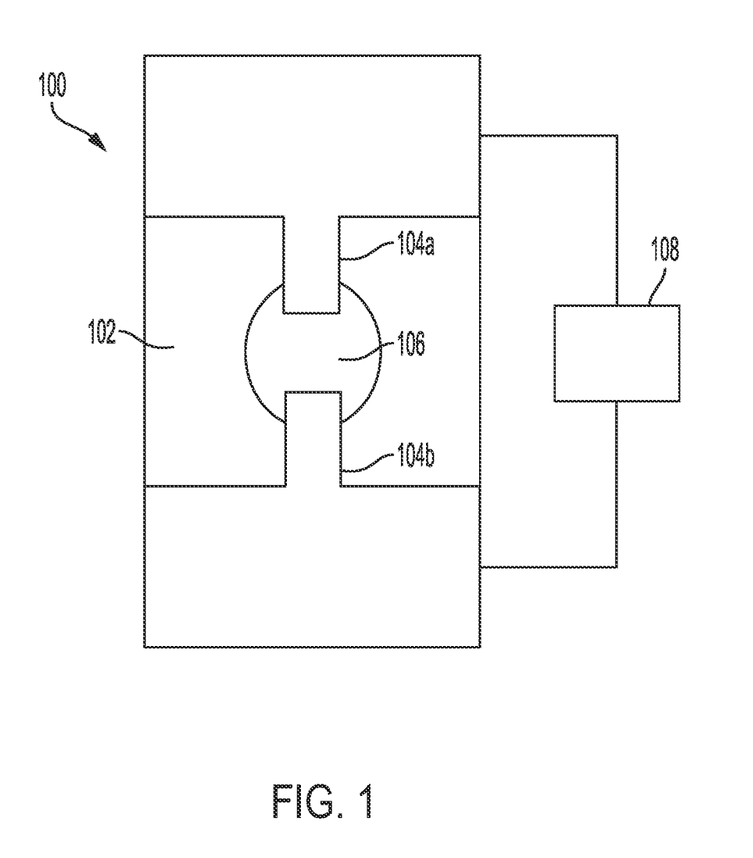
FIG. 1 is a diagram of an illustrative gas sensor for detecting formaldehyde in accordance with the present disclosure.

FIG. 1 is a diagram of an illustrative gas sensor 100 for detecting formaldehyde in accordance with the present disclosure. Gas sensor 100 is a chip-style sensor formed on nonconductive substrate 102. Nonconductive substrate 102 may be any suitable support material, including polymers such as polyethylene naphthalate, polyethylene terephthalate, and the like. The surface of substrate 102 may include various electrode array configurations, such as electrodes 104a and 104b, which may be optionally interdigitated (see FIG. 3). Electrodes 104a and 104b may include one or more conductive materials such as, for example, gold, copper, graphite, titanium, silver, or platinum, including any combination, composite, or alloy thereof. Construction of electrodes 104a and 104b upon nonconductive substrate 102 may be performed by various techniques known in the art, such as vacuum deposition, printing, etching, milling, or the like. Although FIG. 1 depicts only electrodes 104a and 104b for clarity, it is to be appreciated that the scope of the present disclosure may include more complex electrode designs such as, for example, interdigitated electrodes and/or three-dimensional electrode arrays containing more than two electrodes.

Electrodes 104a and 104b may form an electrical connection to measurement device 108 that may incorporate components for powering and operating sensor 100, measuring a change in resistance, and optionally determining a formaldehyde concentration. Measurement device 108 of gas sensor 100 may detect formaldehyde on the basis of a change in resistance, but may also include functionality for measuring changes in drain current, threshold voltage, mobility, or changes in a transfer characteristic such as output current as function of input voltage. For example, measurement device may be a voltmeter. Optionally, measurement device 108 may also include one or more processing devices (e.g., a microprocessor, central processing unit, or the like) that may performs various operations, such as applying electrical signals, measuring electrical signals, and converting electrical signals associated with a change in resistance to provide a formaldehyde concentration.

Formaldehyde analyte detection is promoted by sensing element 106, which forms an electrical connection between electrodes 104a and 104b. Sensing element 106 may include an arylphosphine nanomaterial construct prepared by modification of a nanomaterial with one or more arylphosphines. The modification of the nanomaterial with the arylphosphine may be non-covalent and/or covalent. Suitable nanomaterials for modification with arylphosphines include single-walled carbon nanotubes (SWNT), double-walled carbon nanotubes, multi-walled carbon nanotubes, fullerenes, and the like, conductive carbon black, graphenes including graphene particles, graphene ribbons, graphene sheets, reduced graphenes, the like, and combinations thereof. In some embodiments, nanomaterials may include SWNTs formed from rolled single sheets of graphene, with diameters ranging from about 0.3 nm to 10 nm or about 0.4 nm to about 6 nm, with lengths reaching a few microns. In some examples, the single-walled carbon nanotubes may have an aspect ratio in a range of $10^2$ to $10^8$. The length and/or diameter of the single-walled carbon nanotubes can be varied for particular applications.

Modification of the nanomaterials may be non-covalent or covalent in nature. Non-covalent modifications may include π-π bonding of the arylphosphine with the nanomaterial. Such π-π bonding, also referred to as a π-stacking interaction between an aryl group of the aryl phosphine and the nanomaterial, may occur when delocalized π electrons of aromatic ring systems interact interfacially with one another. Such π-π bonding may bond or otherwise anchor the arylphosphine molecule to the surface (and electrical environment) of the nanomaterial, even without covalent bond formation taking place. As discussed below, arylphosphines may optionally also be covalently bound to the nanomaterial as well.

In addition to the arylphosphines, the nanomaterial may be unmodified (i.e., pristine or substantially pristine) or covalently modified with various functional groups (e.g., carboxylic acid or hydroxyl groups). Such functional groups and others may optionally be further functionalized to promote covalent bonding of the arylphosphine to the nanomaterial, such as through formation of linking groups including, for example, esters, thioesters, ethers, thioethers, carbamates, amides, imines, amidines, aminotoluidines, hydrazones, phosphorothioates, phosphorodithioates, sulfonamides, sulfonates, sulfones, sulfoxides, ureas, thioureas, hydrazides, organosilicon groups, and the like. In some embodiments, covalent modification of the nanomaterial may be minimal, such that the electronic structure of the nanomaterial remains sufficiently undisturbed to remain functional as a sensing element. Direct covalent bonding between carbon and phosphorus may be desirable in some instances, however.

Covalent modification of the nanomaterial may also include direct attachment of arylphosphines to nanomaterial carbons using any suitable method known in the art for generating phosphorus-carbon or carbon-carbon bonds. In some embodiments, covalent modification may include a Friedel-Crafts reaction in which trichlorophosphine is bound to the nanomaterial surface, followed by the exchange of chlorine substituents for alkyl or aryl groups, such as that described in Wu, Y. Y., Wang, L. S., &. Wang, Z. W. (2005). Synthesis of dichlorophenylphosphine via a Friedel-Crafts reaction in [Et4N] Br-XAlCl3 ionic liquids. *Phosphorus, Sulfur, and Silicon*, 180(12), 2667-2677. In other embodiments, covalent modification may involve covalent bond formation between the nanomaterial and one or more carbon substituents of the arylphosphine.

Arylphosphines suitable for use in the disclosure herein are not believed to be particularly limited, provided that the arylphosphines are sufficiently stable for exposure to the environment in which formaldehyde detection is required. Phosphines, including arylphosphines, may be subject to oxidation and conversion to the corresponding phosphine oxide, which reduces their nucleophilicity and overall functionality to promote formaldehyde detection. In addition to substituents that promote non-covalent or covalent anchoring to a nanomaterials, arylphosphines suitable for use in the disclosure herein may also include one or more bulky substituents provide steric hindrance for oxygen access to the phosphorus atom. Bulky substituents may include bulky or branched hydrocarbyl groups, such as cycloalkyl groups (including polycyclic compounds) or branched alkyl groups. Thus, in at least some embodiments, in addition to the at least one aryl group, suitable arylphosphines may include at least one cycloalkyl or branched alkyl group. Suitable cycloalkyl or branched alkyl groups that may be present include, but are not limited to, cyclohexyl, cyclooctyl, t-butyl, neopentyl, and the like.

Arylphosphines disclosed herein may include at least one aryl group, including single and multi-ring aromatic substituents. In at least some embodiments, the at least one aryl group may be a phenyl group, which may be substituted or unsubstituted. Suitable arylphosphines may have a formula of $PR^1R^2R^3$. $R^1$ is selected from $C_1$-$C_{20}$ alkyl groups such as methyl, ethyl, n-propyl, n-butyl, pentyl, hexyl, octyl, and the like; branched alkyl groups such as isopropyl, isobutyl, sec-butyl, tert-butyl, iso-amyl, neopentyl, and the like; $C_1$-$C_{20}$ alkenyl groups having one or more points of unsaturation; $C_1$-$C_{20}$ cycloalkyl groups such as cyclopropyl, cyclobutyl, cyclopentyl, cyclohexyl, cyclooctyl, and the like; $C_1$-$C_{20}$ heterocycles and aromatic heterocycles such as aziridinyl, oxiranyl, thiiranyl, azetidinyl, oxetanyl, thietanyl, thiophenyl, furyanyl, tetrahydrothienyl, tetrahydrofuranyl, pyrrolinyl, pyrrolidinyl, imidazolinyl, imidazolidinyl, oxazolinyl, isoxazolinyl oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, pyridinyl, pyrazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, pyrimidinyl, pyridazinly, morpholinyl, thiomorpholinyl, azepanyl, diazepanyl, azepinyl, oxepanyl, azocanyl, diazocanyl and the like. Any of the foregoing may be optionally substituted.

$R^2$ is an aromatic group, including $C_6$ to $C_{20}$ aromatic groups such as phenyl, benzyl, alkylaryl, fused ring systems such as naphthalene, anthracene, phenanthrene, pyrene, benz(a)anthracene, tetracene, benzo[a]pyrene, benzo[e]pyrene, benzo(g,h,i)perylene, chrysene, dibenz(a,h)anthracene, and the like, any of which may be optionally substituted. In some embodiments, $R^2$ may be the nanomaterial directly bonded to the phosphorus atom of the arylphosphine (e.g., with a direct carbon-phosphorus covalent bond). Even when directly covalently bonded to the phosphorus atom, the carbon nanomaterial may continue to interact by π pi bonding with the arylphosphine as well. Direct covalent bonding of this type may afford a better signal due to the alteration of the π electrons when forming a covalent bond.

$R^3$ is a $C_1$ to $C_{20}$ alkyl, branched alkyl, cycloalkyl group, aromatic or non-aromatic heterocycle, or a $C_6$ to $C_{20}$ aryl group, including any group described above for $R^1$ or $R^2$. In some embodiments, the arylphosphine may comprise at least one phenyl group and/or at least one cyclohexyl group. In some embodiments, the arylphosphine may comprise cyclohexyldiphenylphosphine.

The nanomaterial and the arylphosphine may be present in various mass ratios. In non-limiting embodiments, a mass ratio of arylphosphine:nanomaterial (e.g., single-walled carbon nanotubes) may range from about 4:1 to about 1:10.

Methods for constructing a gas sensor for detecting formaldehyde may comprise: combining an arylphosphine with a suspension of single-walled carbon nanotubes to produce an arylphosphine nanomaterial construct; and depositing the arylphosphine nanomaterial construct between a first electrode and a second electrode. Any suitable technique for forming the first electrode and the second electrode and depositing the arylphosphine nanomaterial construct in between may be utilized in the disclosure herein.

Figure 2:
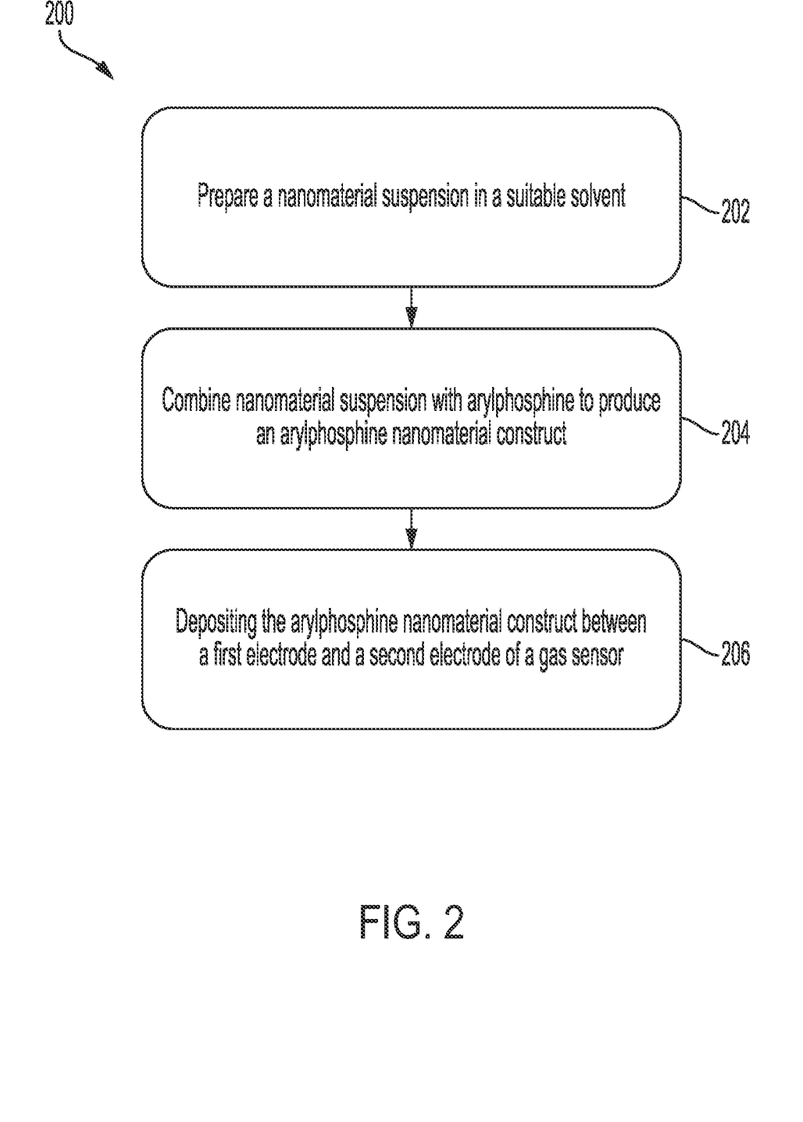
FIG. 2 is a flow diagram of a method to produce a gas sensor for detecting formaldehyde in accordance with the present disclosure.

In non-limiting embodiments, depositing the arylphosphine nanomaterial construct between the first and second electrodes may take place through a printing operation, such as an inkjet printing operation. FIG. 2 is a flow diagram of printing method 200 to produce a gas sensor for detecting formaldehyde in accordance with the present disclosure. At operation 202, a nanomaterial suspension is produced by dispersion of the nanomaterial in a suitable solvent. Nanomaterial suspensions may be formed in various solvents through sonication, vortexing, or other process to aid mixing. Solvents for preparing carbon nanotube suspensions may include, but are not limited to, dimethylformamide; N-methylformamide; N,N-dimethyl acetamide, N-methyl pyrrolidone; $C_2$ to $C_{10}$ alcohols such as ethanol, 1-propanol, isopropanol, 2-ethoxyethanol, and the like; acetophenone; acetone; dimethyl sulfoxide; acrylonitrile; acetonitrile; polyoxymethylene; gamma-butyrolactone; triacetin; the like; and any combination thereof. Nanomaterial suspensions may have a nanomaterial concentration in a range of about 1 mg/mL to about 10 mg/mL.

At operation 204, the nanomaterials are functionalized by combining the nanomaterial suspension with one or more arylphosphines. Nanomaterial suspensions may include a mass ratio of arylphosphine:nanomaterial (e.g., single-walled carbon nanotubes) of about 4:1 to about 1:10, or about 6:1 to about 1:15, or about 8:1 to about 1:20. Increased concentrations of arylphosphines may increase the degree of functionalization (surface coverage) upon the nanomaterials, and may vary depending on the nature of how the arylphosphine is associated with the nanomaterial, how robustly the arylphosphine is associated with the nanomaterial, and the concentration regime of formaldehyde being sensed, for example.

At operation 206, the arylphosphine nanomaterial constructs are printed as an ink composition between at least two electrodes of a sensor (e.g., electrodes 104a and 104b in FIG. 1) to form a sensing element for detecting formaldehyde. Following printing, the arylphosphine nanomaterial constructs form overlapping conductive networks that complete a circuit between the electrodes. Traces of solvent may evaporate naturally following printing or, in some cases, under the application of heat to the sensor. Other suitable methods of depositing arylphosphine nanomaterial constructs between the electrodes may include solid transfer, spraying, chemical vapor deposition (CVD) growth or drop-casting, pipetting, spin-coating, dip-coating, and the like.

As indicated above, the sensors described herein may be utilized for detecting formaldehyde gas under a range of conditions. Such detection methods may comprise: exposing a sensor of the present disclosure to a formaldehyde-containing gas; monitoring a resistance between the first electrode and the second electrode; and determining a formaldehyde concentration from the resistance. As discussed herein, the sensor may comprise a first electrode and a second electrode; and an arylphosphine nanomaterial construct disposed between the first electrode and the second electrode, in which the arylphosphine nanomaterial construct comprises single-walled carbon nanotubes and an arylphosphine comprising at least one aryl group.

In more particular examples, the formaldehyde concentration may be determined based upon a decrease in resistance of the sensor. That is, the measured resistance when the sensor is exposed to a formaldehyde-containing gas may be compared against a baseline, higher resistance measured when the sensor is not being exposed to the formaldehyde-containing gas. The resistance or decrease in resistance may be directly processed by the sensor to provide the formaldehyde concentration, or the resistance or decrease in resistance may be processed offline, either manually or with a separate processing device, to determine the formaldehyde concentration. Determination of the formaldehyde concentration may be performed by correlating the resistance or decrease in resistance against values in a lookup table or database, or by utilizing a calibration curve showing the variance of resistance against known formaldehyde concentrations.

Embodiments disclosed herein include:

A. Sensors for detecting a formaldehyde-containing gas, the sensor comprising: a first electrode and a second electrode; and an arylphosphine nanomaterial construct disposed between the first electrode and the second electrode, the arylphosphine nanomaterial construct comprising: single-walled carbon nanotubes; and an arylphosphine comprising at least one aryl group.

B. Methods for constructing a gas sensor for detecting formaldehyde, comprising: combining an arylphosphine with a suspension of single-walled carbon nanotubes to produce an arylphosphine nanomaterial construct; and depositing the arylphosphine nanomaterial construct between a first electrode and a second electrode.

C. Methods for detecting formaldehyde, comprising: exposing a sensor to a formaldehyde-containing gas, the sensor comprising: a first electrode and a second electrode; and an arylphosphine nanomaterial construct disposed between the first electrode and the second electrode, the arylphosphine nanomaterial construct comprising: single-walled carbon nanotubes; and an arylphosphine comprising at least one aryl group; monitoring a resistance between the first electrode and the second electrode; and determining a formaldehyde concentration from the resistance.

Embodiments A, B and/or C may have one or more of the following additional elements in any combination:

Element 1: wherein the arylphosphine is non-covalently associated with the single-walled carbon nanotubes.

Element 2: wherein the arylphosphine is represented by a formula $PR^1R^2R^3$, wherein $R^1$ is a $C_1$ to $C_{20}$ alkyl, branched alkyl, cycloalkyl, heterocyclic, aromatic heterocyclic group; $R^2$ is a $C_6$ to $C_{20}$ aryl group or the single-walled carbon nanotube; and $R^3$ is a $C_1$ to $C_{20}$ alkyl, branched alkyl, cycloalkyl, heterocyclic, aromatic heterocyclic group, or a $C_6$ to $C_{20}$ aryl group.

Element 3: wherein at least one of $R^1$ and $R^3$ is a cyclohexyl group.

Element 4: wherein $R^2$ is a phenyl group.

Element 5: wherein the arylphosphine is cyclohexyldiphenylphosphine.

Element 6: wherein the sensor is capable of detecting formaldehyde at a concentration ranging from about 50 ppb to about 800 ppb.

Element 7: wherein a resistance of the sensor decreases upon exposure to formaldehyde.

Element 8: wherein a mass ratio of arylphosphine:single-walled carbon nanotubes ranges from about 4:1 to about 1:10.

Element 9: wherein the sensor is capable of detecting formaldehyde at a relative humidity of about 20% or greater at room temperature.

Element 10: wherein the first electrode and the second electrode are interdigitated.

Element 11: wherein one or more of the first electrode and the second electrode comprise a metal deposited on a plastic substrate.

Element 12: wherein a mass ratio of arylphosphine:single-walled carbon nanotubes ranges from about 4:1 to about 1:10.

Element 13: wherein depositing the arylphosphine nanomaterial construct comprises printing by inkjet.

Element 14: wherein the sensor is capable of detecting formaldehyde at concentration ranging from about 50 ppb to about 800 ppb.

Element 15: wherein the sensor is capable of detecting formaldehyde at a relative humidity of about 20% or greater at room temperature.

Element 16: wherein the formaldehyde concentration is determined from a decrease in the resistance.

Element 17: wherein the arylphosphine is cyclohexyldiphenylphosphine.

By way of non-limiting example, exemplary combinations applicable to A include, but are not limited to, 1 and any one or more of 2 to 10; 2 and any one or more of 1 and 3 to 10; 3 and any one or more of 1 to 2 and 4 to 10; 4 and any one or more of 1 to 3 and 5 to 10; 5 and any one or more of 1 to 4 and 6 to 10; 6 and any one or more of 1 to 5 and 7 to 10; 7 and any one or more of 1 to 6 and 8 to 10; 8 and any one or more of 1 to 7 and 9 to 10; 9 and any one or more of 1 to 8 and 10; and 10 and any one or more of 1 to 9. Exemplary combinations applicable to B include, but are not limited to, 11 and any one or more of 12 to 13; 12 and any one or more of 11 or 13; and 13 and any one or more of 11 to 12. Exemplary combinations applicable to C include, but are not limited to, 14 and any one or more of 15 to 17; 15 and any one or more of 14 or 16 to 17; 16 and any one or more of 14 to 15 or 17; and 17 and any one or more of 14 to 16.

To facilitate a better understanding of the present disclosure, the following examples of preferred or representative embodiments are given. In no way should the following examples be read to limit, or to define, the scope of the invention.

EXAMPLES

In the following example, a gas sensor for formaldehyde was constructed using an arylphosphine nanomaterial construct, and various concentrations of formaldehyde were measured therewith. A suspension of single-walled carbon nanotubes was first prepared at a concentration of approximately 1-10 mg/mL in dimethylformamide, and the arylphosphine nanomaterial construct was prepared by combining cyclohexyldiphenylphosphine with the suspension at a mass ratio of at least 4:1 arylphosphine:carbon nanotubes. The suspension containing the arylphosphine nanomaterial construct was used directly for forming the sensor through a printing process.

Figure 3:
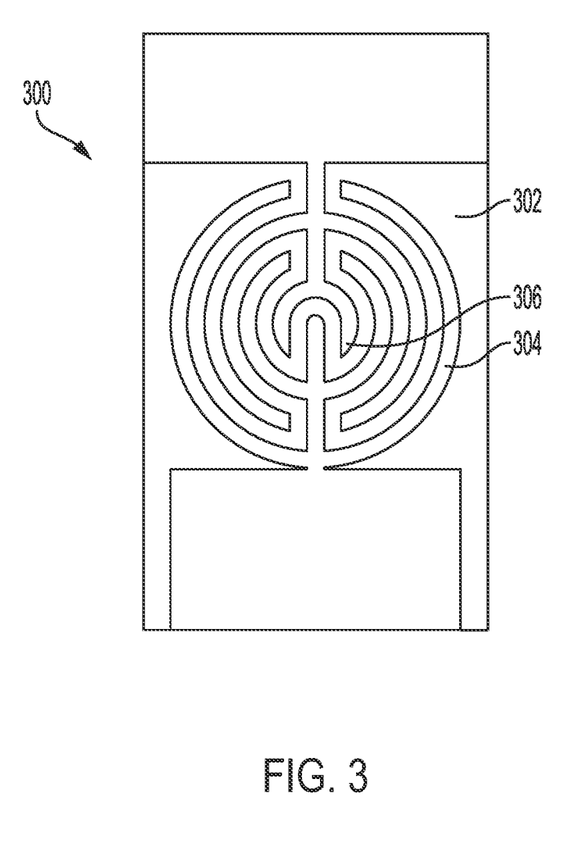
FIG. 3 is an example design of a gas sensor for detecting formaldehyde in accordance with the present disclosure.

FIG. 3 is an example design of gas sensor 300 for detecting formaldehyde in accordance with the present disclosure. As shown, sensor 300 is a chip-style sensor constructed from a flexible polyethylene naphthalate substrate 302 onto which an interdigitated electrode array 304 was patterned by vacuum deposition of gold to a thickness of about 200 nm. Gas sensor 300 was then completed by inkjet printing the arylphosphine nanomaterial construct to afford sensing element 306 between the gold electrodes of electrode array 304, and the solvent was allowed to evaporate.

Figure 4:
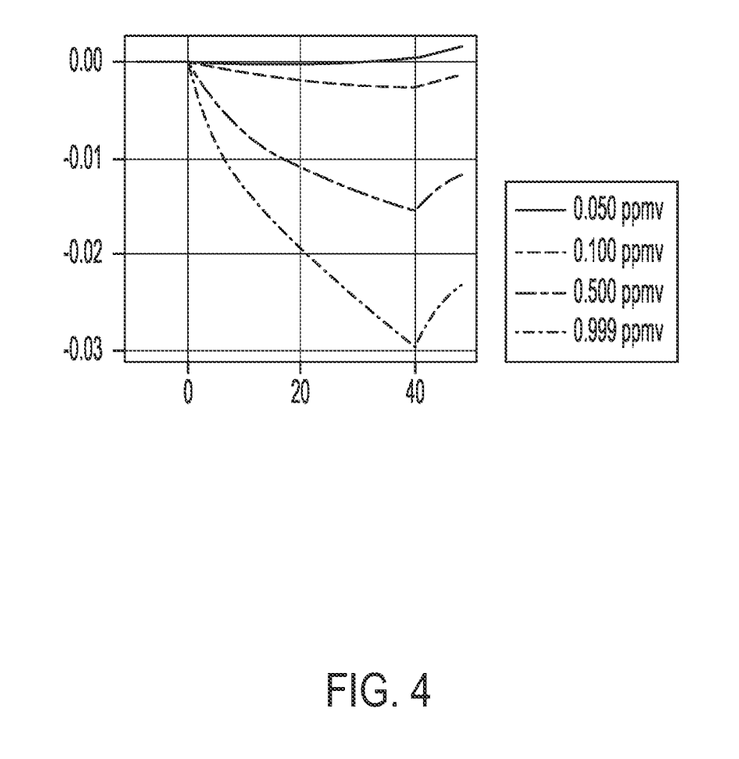
FIG. 4 is a graphical representation of change in resistance as a function of time for a gas sensor when exposed to formaldehyde analyte.

Gas sensor 300 was then tested by measuring the resistance response of the sensor as a function of time when exposed to various concentrations of formaldehyde gas at 30° C. and a RH of 22%. FIG. 4 is a graphical representation of resistance as a function of time (minutes) for the gas sensor when exposed to formaldehyde concentrations of 0.05 ppm, 0.1 ppm, 0.5 ppm, and 0.999 ppm. At time t=0, the sensors are exposed to formaldehyde gas and detection is indicated by an observed decrease in resistance. After 40 minutes, gas exposure is halted, and resistance begins to increase. At higher formaldehyde concentrations, the magnitude of change of resistance is correspondingly higher. Results indicated good sensitivity at all measured formaldehyde concentrations.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is:

1. A sensor for detecting a formaldehyde-containing gas, the sensor comprising:
   a first electrode and a second electrode; and
   an arylphosphine nanomaterial construct disposed between the first electrode and the second electrode, the arylphosphine nanomaterial construct comprising:
   single-walled carbon nanotubes; and
   an arylphosphine comprising at least one aryl group.

2. The sensor of claim 1, wherein the arylphosphine is non-covalently associated with the single-walled carbon nanotubes.

3. The sensor of claim 1, wherein the arylphosphine is represented by a formula $PR^1R^2R^3$, wherein $R^1$ is a $C_1$ to $C_{20}$ alkyl, branched alkyl, cycloalkyl, heterocyclic, or aromatic heterocyclic group; R2 is a $C_6$ to $C_{20}$ aryl group or the single-walled carbon nanotubes; and $R^3$ is a $C_1$ to $C_{20}$ alkyl, branched alkyl, cycloalkyl, heterocyclic, or aromatic heterocyclic group, or a $C_6$ to $C_{20}$ aryl group.

4. The sensor of claim 3, wherein at least one of $R^1$ and $R^3$ is a cyclohexyl group.

5. The sensor of claim 3, wherein $R^2$ is a phenyl group.

6. The sensor of claim 1, wherein the arylphosphine is cyclohexyldiphenylphosphine.

7. The sensor of claim 1, wherein the sensor is capable of detecting formaldehyde at a concentration ranging from about 50 ppb to about 800 ppb.

8. The sensor of claim 1, wherein a resistance of the sensor decreases upon exposure to formaldehyde.

9. The sensor of claim 1, wherein a mass ratio of arylphosphine:single-walled carbon nanotubes ranges from about 4:1 to about 1:10.

10. The sensor of claim 1, wherein the sensor is capable of detecting formaldehyde at a relative humidity of about 20% or greater at room temperature.

11. The sensor of claim 1, wherein the first electrode and the second electrode are interdigitated.

12. A method for constructing a gas sensor for detecting formaldehyde, comprising:
    combining an arylphosphine with a suspension of single-walled carbon nanotubes to produce an arylphosphine nanomaterial construct; and
    depositing the arylphosphine nanomaterial construct between a first electrode and a second electrode.

13. The method of claim 12, wherein one or more of the first electrode and the second electrode comprise a metal deposited on a plastic substrate.

14. The method of claim 12, wherein a mass ratio of arylphosphine:single-walled carbon nanotubes ranges from about 4:1 to about 1:10.

15. The method of claim 12, wherein depositing the arylphosphine nanomaterial construct comprises printing by inkjet.

16. A method for detecting formaldehyde, comprising:
    exposing a sensor to a formaldehyde-containing gas, the sensor comprising:
    a first electrode and a second electrode; and
    an arylphosphine nanomaterial construct disposed between the first electrode and the second electrode, the arylphosphine nanomaterial construct comprising:
    single-walled carbon nanotubes; and
    an arylphosphine comprising at least one aryl group;
    monitoring a resistance between the first electrode and the second electrode; and
    determining a formaldehyde concentration from the resistance.

17. The method of claim 16, wherein the sensor is capable of detecting formaldehyde at concentration ranging from about 50 ppb to about 800 ppb.

18. The method of claim 16, wherein the sensor is capable of detecting formaldehyde at a relative humidity of about 20% or greater at room temperature.

19. The method of claim 16, wherein the formaldehyde concentration is determined from a decrease in the resistance.

20. The method of claim 16, wherein the arylphosphine is cyclohexyldiphenylphosphine.

* * * * *